(12) United States Patent
Christian

(10) Patent No.: US 8,979,840 B2
(45) Date of Patent: Mar. 17, 2015

(54) IRRIGANT DISTRIBUTION SYSTEM FOR FLEXIBLE ELECTRODES

(75) Inventor: Steven C. Christian, New Brighton, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 903 days.

(21) Appl. No.: 13/162,417

(22) Filed: Jun. 16, 2011

(65) Prior Publication Data

US 2012/0157991 A1    Jun. 21, 2012

Related U.S. Application Data

(63) Continuation-in-part of application No. 12/971,645, filed on Dec. 17, 2010, now Pat. No. 8,814,857, and a continuation-in-part of application No. 13/151,750, filed on Jun. 2, 2011, which is a continuation-in-part of application No. 12/979,803, filed on Dec. 28, 2010.

(51) Int. Cl.
*A61B 18/18* (2006.01)
*A61B 18/14* (2006.01)
(Continued)

(52) U.S. Cl.
CPC .............. *A61B 18/1492* (2013.01); *A61B 18/02* (2013.01); *A61B 2017/00323* (2013.01);
(Continued)

(58) Field of Classification Search
CPC ............... A61B 18/1492; A61B 18/02; A61B 2017/00323; A61B 2018/00702; A61B 18/00791; A61B 18/00345; A61B 18/00029; A61B 18/00744; A61B 18/00863; A61B 18/1965; A61B 18/00577; A61B 2218/002
USPC ...................................... 606/33–52
See application file for complete search history.

(56) References Cited

U.S. PATENT DOCUMENTS 5,290,263 A    3/1994 Wigness et al.
5,348,554 A    9/1994 Imran et al.
(Continued)

FOREIGN PATENT DOCUMENTS

JP    2010-505596 A    2/2010
WO    2008/045925 A2    4/2008
(Continued)

OTHER PUBLICATIONS

"International Search Report and Written Opinion", PCT/US2011/059111, Apr. 13, 2012.
(Continued)

*Primary Examiner* — Linda Dvorak
*Assistant Examiner* — Amanda Scott
(74) *Attorney, Agent, or Firm* — Dykema Gossett PLLC

(57) ABSTRACT

Ablation electrode assemblies having a longitudinal axis include an electrode core member; an electrode shell; and an irrigant distribution element. The electrode core member comprises a thermal insulator and has a first end; a second end; and at least one irrigation passageway. The electrode shell comprises an electrically conductive material, defines an inner volume, and has a first end; and a second end. The second end of the electrode shell is configured for connection to the first end of the electrode core member. The electrode shell is sufficiently flexible for deflection of the distal end of the electrode shell relative to the longitudinal axis of the ablation electrode assembly. The irrigant distribution assembly comprises a first end; and a second end, wherein the second end of the irrigant distribution element defines a circumferential irrigation port between the irrigant distribution element and the electrode core member.

26 Claims, 9 Drawing Sheets

(51) Int. Cl.
    *A61B 18/02*      (2006.01)
    *A61B 17/00*      (2006.01)
    *A61B 18/00*      (2006.01)
    *A61N 7/02*       (2006.01)

(52) U.S. Cl.
    CPC .............. *A61B 2018/00345* (2013.01); *A61B 2018/00702* (2013.01); *A61B 2018/00791* (2013.01); *A61B 2218/002* (2013.01); *A61N 7/022* (2013.01)
    USPC ........................................... 606/41; 606/42

(56) References Cited

U.S. PATENT DOCUMENTS

| | | | |
|---|---|---|---|
| 5,688,267 A | 11/1997 | Panescu et al. | |
| 5,735,846 A | 4/1998 | Panescu et al. | |
| 5,792,140 A | 8/1998 | Tu et al. | |
| 5,897,552 A * | 4/1999 | Edwards et al. | 606/31 |
| 6,010,500 A | 1/2000 | Sherman et al. | |
| 6,017,338 A | 1/2000 | Brucker et al. | |
| 6,068,653 A * | 5/2000 | LaFontaine | 607/116 |
| 6,233,476 B1 | 5/2001 | Strommer et al. | |
| 6,498,944 B1 | 12/2002 | Ben-Haim et al. | |
| 6,506,189 B1 | 1/2003 | Rittman et al. | |
| 6,522,930 B1 | 2/2003 | Schaer et al. | |
| 6,575,969 B1 | 6/2003 | Rittman et al. | |
| 6,579,288 B1 | 6/2003 | Swanson et al. | |
| 6,616,655 B1 | 9/2003 | Falwell et al. | |
| 6,690,963 B2 | 2/2004 | Ben-Haim et al. | |
| 6,788,967 B2 | 9/2004 | Ben-Haim et al. | |
| 6,936,047 B2 | 8/2005 | Nasab et al. | |
| 7,197,354 B2 | 3/2007 | Sobe | |
| 7,263,397 B2 | 8/2007 | Hauck et al. | |
| RE39,863 E | 10/2007 | Smith | |
| 7,344,533 B2 | 3/2008 | Pearson et al. | |
| 7,386,339 B2 | 6/2008 | Strommer et al. | |
| 7,389,148 B1 * | 6/2008 | Morgan | 607/116 |
| 7,536,218 B2 | 5/2009 | Govari et al. | |
| 7,591,816 B2 | 9/2009 | Wang et al. | |
| 7,776,034 B2 | 8/2010 | Kampa | |
| 7,815,635 B2 | 10/2010 | Wittkampf et al. | |
| 7,824,406 B2 | 11/2010 | Wang et al. | |
| 7,826,905 B2 | 11/2010 | Chitre et al. | |
| 2003/0004506 A1 | 1/2003 | Messing | |
| 2003/0060822 A1 | 3/2003 | Schaer et al. | |
| 2003/0195510 A1 * | 10/2003 | Schaer | 606/41 |
| 2005/0090816 A1 | 4/2005 | McClurken et al. | |
| 2006/0287650 A1 | 12/2006 | Cao et al. | |
| 2007/0043349 A1 | 2/2007 | Swanson et al. | |
| 2007/0049915 A1 | 3/2007 | Haemmerich et al. | |
| 2007/0270791 A1 | 11/2007 | Wang et al. | |
| 2008/0065062 A1 | 3/2008 | Leung et al. | |
| 2008/0071267 A1 | 3/2008 | Wang et al. | |
| 2008/0091193 A1 | 4/2008 | Kauphusman et al. | |
| 2008/0161795 A1 | 7/2008 | Wang et al. | |
| 2008/0167646 A1 * | 7/2008 | Godara et al. | 606/41 |
| 2009/0125016 A1 | 5/2009 | Wang et al. | |
| 2009/0125017 A1 | 5/2009 | Wang et al. | |
| 2009/0163911 A1 | 6/2009 | Cao et al. | |
| 2009/0163913 A1 | 6/2009 | Wang et al. | |
| 2009/0171187 A1 * | 7/2009 | Gerhart et al. | 600/421 |
| 2009/0171188 A1 | 7/2009 | Paul et al. | |
| 2009/0177193 A1 * | 7/2009 | Wang et al. | 606/33 |
| 2009/0240248 A1 * | 9/2009 | Deford et al. | 606/41 |
| 2009/0240249 A1 * | 9/2009 | Chan et al. | 606/41 |
| 2009/0312756 A1 | 12/2009 | Schlesinger et al. | |
| 2010/0069921 A1 | 3/2010 | Miller et al. | |
| 2010/0137859 A1 | 6/2010 | Wang | |
| 2010/0152727 A1 | 6/2010 | Gibson et al. | |
| 2010/0152731 A1 | 6/2010 | de la Rama et al. | |
| 2010/0168729 A1 | 7/2010 | Wang et al. | |
| 2010/0168736 A1 | 7/2010 | Wang | |
| 2010/0174177 A1 | 7/2010 | Wu | |
| 2011/0092969 A1 | 4/2011 | Wang et al. | |
| 2011/0264089 A1 | 10/2011 | Zirkle et al. | |
| 2012/0035605 A1 | 2/2012 | Tegg et al. | |

FOREIGN PATENT DOCUMENTS

| | | |
|---|---|---|
| WO | 2008082988 | 10/2008 |
| WO | 2008083000 | 10/2008 |
| WO | 2008083003 | 10/2008 |
| WO | 2009082574 | 2/2009 |
| WO | 2009070446 | 4/2009 |

OTHER PUBLICATIONS

International Search Report and Written Opinion of ISA for PCT/US2012/023355 mailed Jun. 4, 2012.
International Search Report and Written Opinion of ISA for PCT/US2012/026759 mailed Jul. 5, 2012.

* cited by examiner

IRRIGANT DISTRIBUTION SYSTEM FOR FLEXIBLE ELECTRODES

CROSS-REFERENCE TO RELATED APPLICATIONS

This application is a continuation-in-part of U.S. patent application Ser. No. 13/151,750 entitled "Multi-rate Fluid Flow and Variable Power Delivery for Ablation Electrode Assemblies Used in Catheter Ablation Procedures," filed 2 Jun. 2011 (the '750 application), which is a continuation-in-part of U.S. patent application Ser. No. 12/979,803 entitled "Ablation Electrode Assemblies and Methods for Using Same," filed 28 Dec. 2010 (the '803 application), now pending; and this application is a continuation-in-part of U.S. patent application Ser. No. 12/971,645 entitled "Irrigated Ablation Electrode Assemblies," filed 17 Dec. 2010 (the '645 application), now U.S. Pat. No. 8,814,857. The '750 application, the '803 application, and the '645 application are all hereby incorporated by reference in their entirety as though fully set forth herein.

BACKGROUND OF THE INVENTION a. Field of the Invention

The instant disclosure relates generally to ablation electrode assemblies including a flexible electrode shell and an irrigant distribution element.

b. Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include, for example, radio frequency (RF) ablation, cryoablation, laser ablation, chemical ablation, high-intensity focused ultrasound-based ablation, microwave ablation. An electrophysiology catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

During RF ablation, local temperature elevation can result in coagulum formation on the ablation electrode, resulting in an impedance rise. As the impedance increases, more energy is passed through the portion of the electrode without coagulation, creating even higher local temperatures and further increasing coagulum formation and the impedance. Finally, enough blood coagulates onto the electrode that no energy passes into the targeted tissue, thereby requiring the catheter to be removed from the vascular system, the electrode to be cleaned, and the catheter to be repositioned within the cardiac system at the desired location. Not only can this process be time consuming, but it can be difficult to return to the previous location because of the reduced electrical activity in the targeted tissue, which has been previously ablated. Recent studies have also demonstrated the formation of a so-called soft thrombus in RF ablation. The formation of the soft thrombus results from heat induced protein denaturation and aggregation and occurs independently of heparin concentration in serum. In addition, RF ablation can generate significant heat, which, if not controlled, can result in excessive tissue damage, such as tissue charring, steam pop, and the like.

Accordingly, it can be desirable to monitor and/or control the temperature of ablation electrode assemblies and/or targeted tissue. Thermal sensors such as thermocouples and/or thermistors may be used to monitor the temperature of ablation electrode assemblies. RF ablation catheters can be configured to provide temperature feedback during RF ablation via the thermal sensors in order to adjust one or more parameters of an RF ablation cycle. Accordingly, it can be desirable to improve temperature correlation between the electrode and tissue interface in order to provide more accurate temperature feedback with respect to the tissue temperature for controlling energy delivery and/or other parameters during an RF ablation cycle. It can also be desirable to use ablation electrode assemblies to provide irrigation fluid during RF ablation. In addition, it can be desirable to provide a flexible electrode that may be better configured to conform to the tissue surface targeted for treatment by deflecting and/or undergoing deformation when the flexible electrode comes into physical contact with the targeted tissue. In this way, a flexible electrode can better accommodate cardiac anatomy, and conformation of the electrode with the cardiac anatomy can ensure more efficient energy delivery.

BRIEF SUMMARY OF THE INVENTION

It is desirable to have improved temperature correlation between the electrode of the ablation electrode assembly and the tissue interface. It is also desirable, in some embodiments, to include a mechanism to irrigate the ablation electrode assemblies and/or targeted areas in a patient's body with biocompatible fluids, such as saline solution, in order to reduce charring and inhibit the formation of coagulum and/or soft thrombus, as well as to enable deeper and/or greater volume lesions as compared to conventional, non-irrigated catheters at identical power settings. This can, in turn, enable greater energy delivery during RF ablation. The flow of biocompatible fluids (i.e., irrigation fluids) can be turbulent in order to provide an enveloping flow pattern adjacent to the surface of the ablation electrode assemblies for mixing with, displacing, and/or diluting blood that can be in contact with the ablation electrode assemblies in order to prevent stasis and the formation of coagulum. In addition, it may be desirable for the electrode to conform to cardiac anatomy in order to improve energy efficiency during RF ablation.

An ablation electrode assembly in accordance with an embodiment of the disclosure has a longitudinal axis, an electrode core member, an electrode shell, and an irrigant distribution element. The electrode core member comprises a thermal insulator having a reduced thermal conductivity. The electrode core member has a first end; a second end; and at least one irrigation passageway. In accordance with an embodiment of the disclosure, the electrode core member further comprises an outer surface and an inner surface defining a cavity. The at least one irrigation passageway extends from the inner cavity to the outer surface of the electrode core member. In accordance with an embodiment of the disclosure, the electrode core member further comprises an axially extending passageway extending from the inner cavity of the electrode core member toward the first end of the electrode shell. The ablation electrode assembly can further include at least one port extending from the axially extending passageway to the first end of the electrode shell, wherein the port is oriented at an acute angle relative to the longitudinal axis of the ablation electrode assembly in accordance with an embodiment of the disclosure. At least a portion of the circumference and at least a portion of the length of the axially extending passageway can include a coating of an electrically non-conductive material.

The electrode shell comprises an electrically conductive material. The electrode shell defines an inner volume and has a first end; and a second end. The second end of the electrode shell is configured for connection to the first end of the electrode core member. The electrode shell is sufficiently flexible for deflection of the distal end of the electrode shell relative to the longitudinal axis of the ablation electrode assembly. The irrigant distribution element has a first end; and a second end. The second end of the irrigant distribution element defines a circumferential irrigation port between the irrigant distribution element and the electrode core member. In accordance with a first embodiment of the disclosure, at least a portion of the electrode shell includes a first set of projections defining at least in part a corresponding first set of recesses, and at least a portion of the electrode shell includes a second set of projections defining at least in part a corresponding second set of recesses. At least one of the first set of projections is configured to interlock with at least one of the second set of recesses, and at least one of the second set of projections is configured to interlock with at least one of the first set of recesses. Each of the first set of projections and each of the second set of projections can be trapezoidal in shape in an embodiment of the disclosure. Each of the first set of projections and each of the second set of projections can be rounded in shape in an embodiment of the disclosure.

In accordance with a second embodiment of the disclosure, the electrode shell can comprise wound or braided metallic wires. In accordance with a third embodiment of the disclosure, the electrode shell can comprise a polymer (for example and without limitation, silicone) having electrically conductive particles dispersed therein at a predefined density to achieve a desired electrical conductivity. The particles can comprise gold, silver, platinum, iridium, titanium, tungsten, or a combination thereof in accordance with various embodiments of the invention.

In accordance with an embodiment of the invention, the ablation electrode assembly can further include a plug disposed within the inner volume defined by the electrode shell. The plug can comprise a polymer (for example and without limitation, a silicone material). The plug can have a predefined durometer to achieve a desired flexibility in accordance with an embodiment of the invention.

The irrigant distribution element can comprise an annular ring and can further comprise a fluid shaping member, such as a channel, rifling, boss, hump, chamfer, or combination thereof, in order to improve fluid flow characteristics of the irrigation fluid.

A system for cardiac ablation of cardiac tissue in accordance with an embodiment of the disclosure includes a catheter, at least one thermal sensor disposed within the catheter, an ablation generator, and an electronic control unit (ECU). The catheter comprises a catheter shaft having a fluid lumen; and an electrode assembly connected to the catheter shaft. The electrode assembly comprises an electrode core member, an electrode shell, and an irrigant distribution element. The electrode core member comprises a thermal insulator having a reduced thermal conductivity. The electrode core member has a first end; a second end; and at least one irrigation passageway. The electrode shell comprises an electrically conductive material. The electrode shell defines an inner volume and has a first end and a second end. The second end of the electrode shell is configured for connection to the first end of the electrode core member. The electrode shell is sufficiently flexible for deflection of the distal end of the electrode shell relative to the longitudinal axis of the ablation electrode assembly. The irrigant distribution element has a first end and a second end, wherein the second end of the irrigant distribution element defines a circumferential irrigation port between the irrigant distribution element and the electrode core member. The ablation generator can be electrically connected to at least a portion of the electrode assembly, and the ECU can be operatively connected to the at least one thermal sensor. The ECU can be configured to receive as an input data from the at least one plurality of thermal sensors and can be configured to control energy delivery and irrigation fluid delivery to the electrode assembly based at least in part on the input data.

DETAILED DESCRIPTION OF THE DISCLOSURE

The instant disclosure generally relates to irrigated ablation electrode assemblies. For purposes of this description, similar aspects among the various embodiments described herein will be referred to by similar reference numbers. As will be appreciated, however, the structure of the various aspects can be different among the various embodiments.

Figure 1:
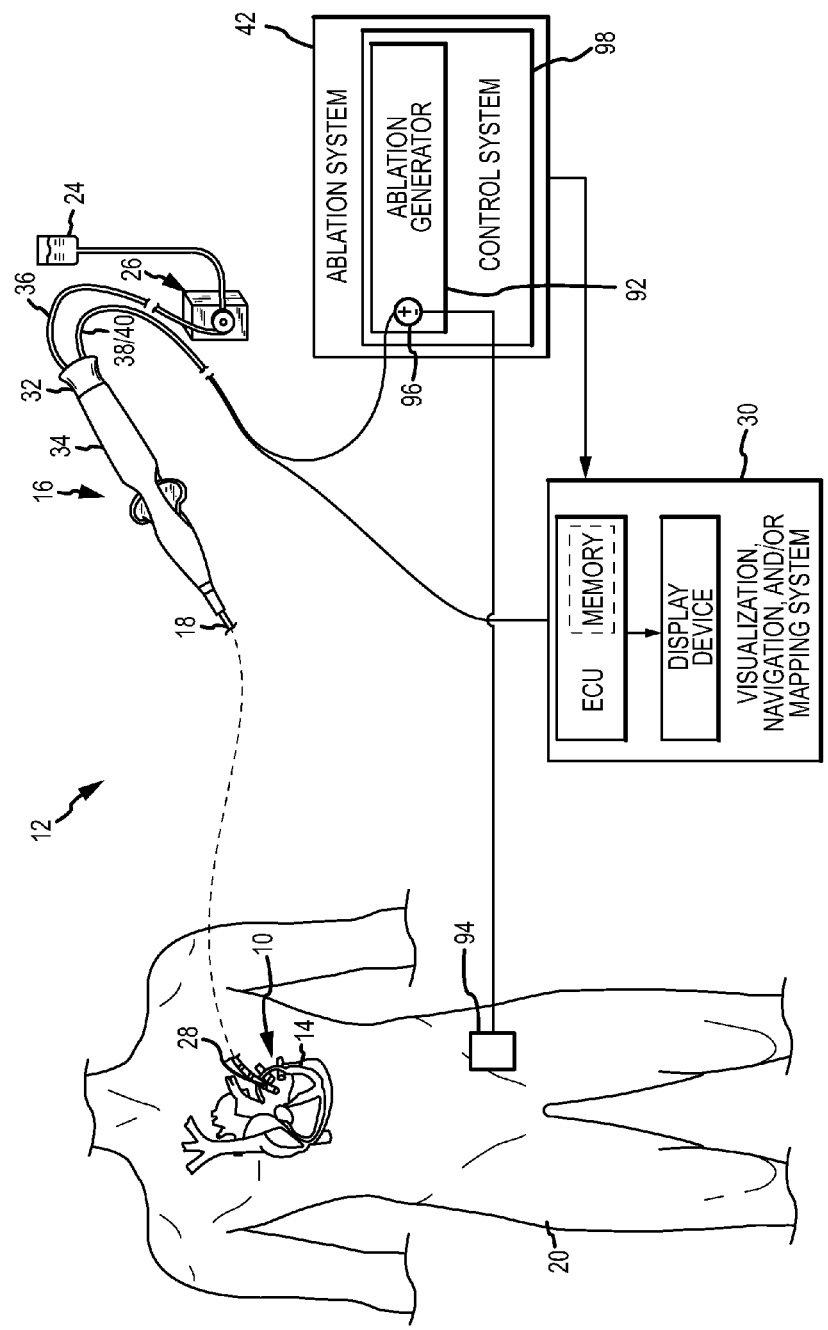
FIG. 1 is a diagrammatic view of a system for performing one more diagnostic and/or therapeutic functions in association with cardiac tissue.

Referring to FIG. 1, an ablation electrode assembly 10 can comprise part of an irrigated catheter system 12 for examination, diagnosis, and/or treatment of internal body tissues (e.g., targeted tissue areas 14). In an exemplary embodiment, the irrigated catheter assembly can comprise an ablation catheter 16 (e.g., radio frequency (RF), cryoablation, ultrasound, etc.). The instant disclosure generally refers to RF ablation electrodes and electrode assemblies, but it is contemplated that the instant disclosure is equally applicable to any number of other ablation electrodes and electrode assemblies where the temperature of the device and of the targeted tissue areas can be factors during diagnostic and/or therapeutic medical procedures.

Still referring to FIG. 1, the irrigated catheter assembly includes a catheter shaft 18 that is an elongate, tubular, flexible member configured for movement within a body. The catheter shaft 18 can be introduced into a blood vessel or other structure within a body 20 through a conventional introducer. The catheter shaft 18 can be steered or guided through a body to a desired location such as targeted tissue areas 14 with pullwires, tension elements, so-called push elements, or other means known in the art.

Figure 2:
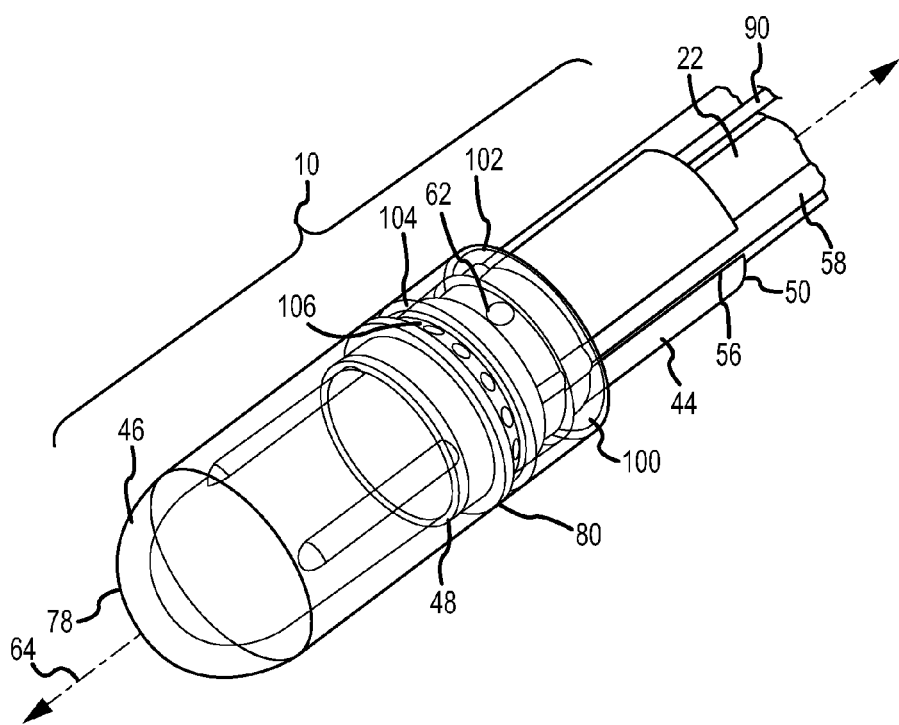
FIG. 2 is an isometric partially transparent view of an ablation electrode assembly in accordance with a first embodiment of the disclosure.

The irrigated catheter assembly further includes at least one fluid lumen or fluid delivery tube 22 disposed within the catheter shaft 18, best shown in FIG. 2. The fluid delivery tube 22 is configured to supply fluid to the ablation electrode assembly 10. Referring now to FIGS. 1-2, the fluid delivery tube 22 of the irrigated catheter assembly can be connected to a fluid source 24 providing a biocompatible fluid such as saline, or a medicament, through a pump 26, which can comprise, for example, a fixed rate roller pump or variable volume syringe pump with a gravity feed supply from the fluid source for irrigation. The fluid source 24 and/or pump 26 is conventional in the art. The fluid source 24 and/or pump 26 can comprise a commercially available unit sold under the name Cool Point™, available from St. Jude Medical, Inc. in an embodiment.

Referring now to FIG. 1, the irrigated catheter assembly can further include one or more positioning electrodes 28 mounted in or on the catheter shaft 18. The electrodes 28 can comprise, for example, ring electrodes. The electrodes 28 can be used, for example, with a visualization, navigation, and mapping system 30. The electrodes 28 can be configured to provide a signal indicative of both a position and orientation of at least a portion of the catheter shaft 18. The visualization, navigation, and/or mapping system 30 with which the electrodes 28 can be used can comprise an electric field-based system, or, sometimes referred to as an impedance based system, such as, for example, that having the model name ENSITE NAVX (aka EnSite Classic as well as newer versions of the EnSite system, denoted as ENSITE VELOCITY) and commercially available from St. Jude Medical, Inc. and as generally shown with reference to U.S. Pat. No. 7,263,397 titled "Method and Apparatus for Catheter Navigation and Location and Mapping in the Heart," the entire disclosure of which is incorporated herein by reference. The visualization, navigation, and/or mapping system 30 can include an electronic control unit (ECU) and display device. The ECU can comprise a programmable microprocessor or microcontroller, but can alternatively comprise an application specific integrated circuit (ASIC). The ECU can include a central processing unit (CPU) and an input/output (I/O) interface through which the ECU can receive input data and can generate output data. The ECU can also have a memory, and the input data and/or output data acquired and generated by the ECU can be stored in the memory of the ECU.

In accordance with an electric field-based system, the electrodes 28 can be configured to be responsive to an electric field transmitted within the body 20 of the patient. The electrodes 28 can be used to sense an impedance at a particular location and transmit a representative signal to an external computer or processor. In other exemplary embodiments, however, the visualization, navigation, and/or mapping system 30 can comprise other types of systems, such as, for example and without limitation: a magnetic field-based system such as the CARTO System (now in a hybrid form with impedance- and magnetically-driven electrodes) available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd. of Haifa, Israel (now owned by St. Jude Medical, Inc.), and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference. In accordance with a magnetic field-based system, the catheter can be configured to include field sensors (e.g., coils) responsive to a magnetic field transmitted through the body 20 of the patient to sense the strength of the field at a particular location and transmit a representative signal to an external computer or processor. Such field sensors can comprise one or more metallic coils located on or within the catheter shaft 18 in a magnetic field-based system. As noted above, a combination electric field-based and magnetic field-based system such as the CARTO 3 System also available from Biosense Webster, and as generally shown with reference to U.S. Pat. No. 7,536,218 entitled "Hybrid Magnetic-Based and Impedance-Based Position Sensing," the entire disclosure of which is incorporated herein by reference, can be used. In accordance with a combination electric field-based and magnetic field-based system, the catheter can include both electrodes 28 as impedance-based electrodes and one or more magnetic field sensing coils. Commonly available fluoroscopic, computed tomography (CT), and magnetic resonance imaging (MRI)-based systems can also be used.

The irrigated catheter assembly can include other conventional components such as, for example and without limitation, conductors associated with the electrodes, and possibly additional electronics used for signal processing, visualization, localization, and/or conditioning. The irrigated catheter assembly can further include multiple lumens for receiving additional components. Still referring to FIG. 1, the irrigated catheter assembly can further include a cable connector or interface 32 and a handle 34. The cable connector or interface 32 can provide mechanical, fluid, and electrical connection(s) for cables 36, 38, 40 extending from the pump 26 and/or an ablation system 42 as described in more detail below. The cable connector or interface 32 can be conventional in the art and can be disposed at the proximal end of the irrigated catheter assembly. The handle 34 can provide a location for the clinician to hold the irrigated catheter assembly and can further provide means for steering or guiding the catheter shaft 18 within the body 20 as known in the art. Catheter handles are generally conventional in the art and it will be understood that the construction of the handle can vary. In an embodiment, for the purpose of steering the catheter shaft 18 within the body 20, the handle 34 can be substituted by a controllable robotic actuator.

Figure 3:
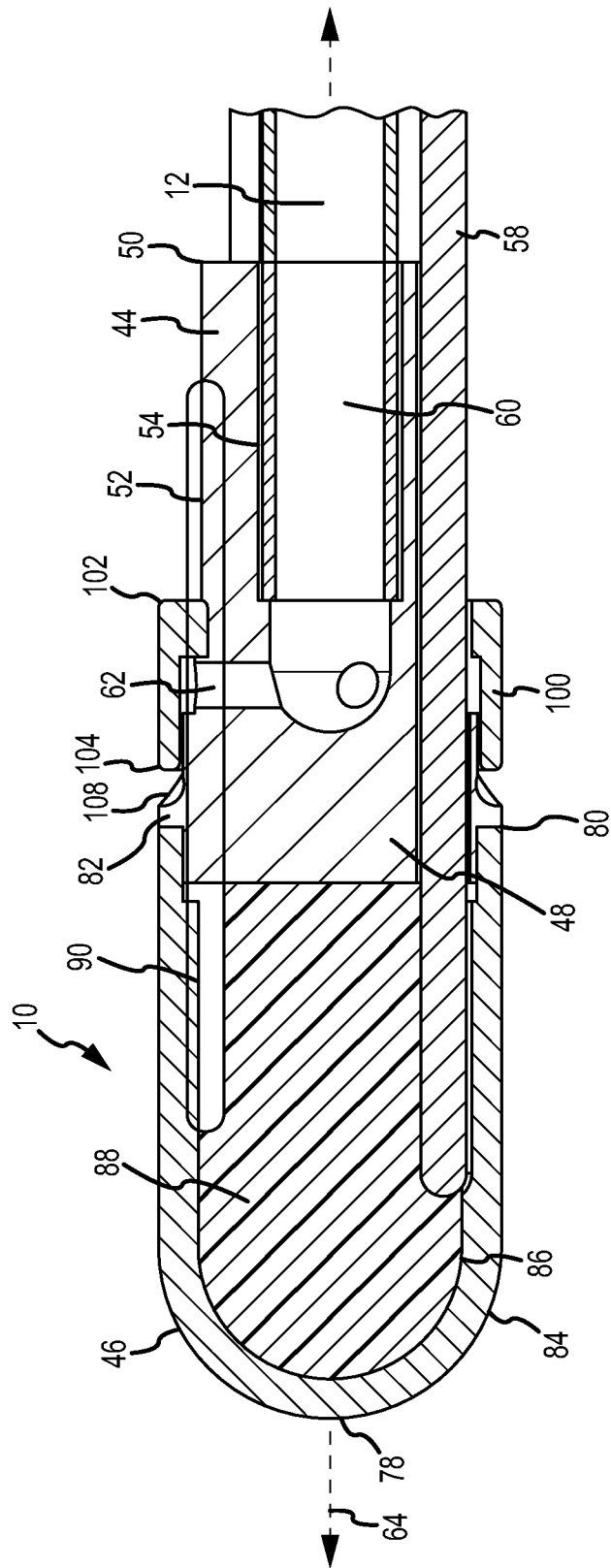
FIG. 3 is a cross-sectional view of the ablation electrode assembly of FIG. 2.

Referring now to FIGS. 1-4, ablation electrode assembly 10 can be connected to and/or coupled with the catheter shaft 18. Ablation electrode assembly 10 can be disposed at or near the distal end of the catheter shaft 18. Ablation electrode assembly 10 can be disposed at the extreme distal end (e.g., tip) of the catheter shaft 18. Referring now to FIGS. 2-3, the ablation electrode assembly 10 can include an electrode core member 44 and an electrode shell 46 in accordance with a first embodiment of the disclosure. The lengths and/or diameters of ablation electrode assembly 10, electrode core member 44, electrode shell 46, as well as portions thereof, can vary depending on the design of ablation electrode assembly 10. The electrode shell 46 can be about four millimeters in length in an embodiment. Although four millimeters is mentioned in detail, the length of the electrode shell 46 can vary in accordance with various embodiments of the invention.

Electrode core member 44 is configured for coupling the ablation electrode assembly 10 to the catheter shaft 18 and for routing various components to the electrode shell 46. Electrode core member 44 has a first end 48 and a second end 50. First end 48 can be a distal end, and second end 50 can be a proximal end in accordance with an embodiment of the disclosure. Electrode core member 44 can be generally cylindrical in shape. The first end 48 of the electrode core member 44 can be generally flat in accordance with an embodiment of the disclosure. The second end 48 of the electrode core member 44 can be partially spherical or generally hemispherical in shape in accordance with other embodiments of the disclosure. Although these particular shapes are mentioned in detail, the shape of the first end 48 of the electrode core member 44 can vary in accordance with various embodiments of the disclosure. The second end 50 of the electrode core member 44 can be configured for coupling and/or connecting electrode core member 44 with the catheter shaft 18. The second end 50 of the electrode core member 44 can also be configured to receive the fluid delivery tube 22. The electrode core member 44 can include multiple lumens for receiving any number of components (e.g., wires and the like) which can be routed through the electrode core member 44. As best illustrated in FIG. 3, the electrode core member 44 also has an outer surface 52 and an inner surface 54. Referring back to FIG. 2, the outer surface 52 of the electrode core member 44 can include at least one channel 56 for receiving a thermal sensor 58.

Accordingly, the ablation electrode assembly 10 can include at least one thermal sensor 58 in accordance with an embodiment of the disclosure as best shown in FIGS. 2-3. The ablation electrode assembly 10 can include three thermal sensors 58 in accordance with an embodiment of the disclosure. The thermal sensors 58 can be substantially equally spaced around the periphery or circumference of the electrode core member 44. Although three sensors that are substantially equally spaced are mentioned in detail, the ablation electrode assembly 10 can include fewer or more thermal sensors 58 in other embodiments and the location of the thermal sensors 58 can vary in other embodiments. For example, in an embodiment, a single thermal sensor 58 may be centered within the ablation electrode assembly 10. Thermal sensors 58 can be connected and/or coupled to electrode core member 44 (and/or ablation electrode assembly 10) in any manner that is conventional in the art to hold thermal sensors 58 in place relative to electrode core member 44 (and/or ablation electrode assembly 10). Thermal sensors 58 are configured for measurement and temperature control/regulation of ablation electrode assembly 10. Thermal sensors 58 can be any mechanism known to one of ordinary skill in the art, including for example and without limitation, thermocouples and/or thermistors. Thermal sensors 58 can comprise other types of devices, such as for example and without limitation, devices for determining pressure, temperature and a flow parameter of a flowing fluid available from Radi Medical Systems AB, and as generally shown with reference to at least U.S. Pat. No. RE39,863 entitled "Combined flow, pressure and temperature sensor," the entire disclosure of which is incorporated herein by reference.

Figure 4:
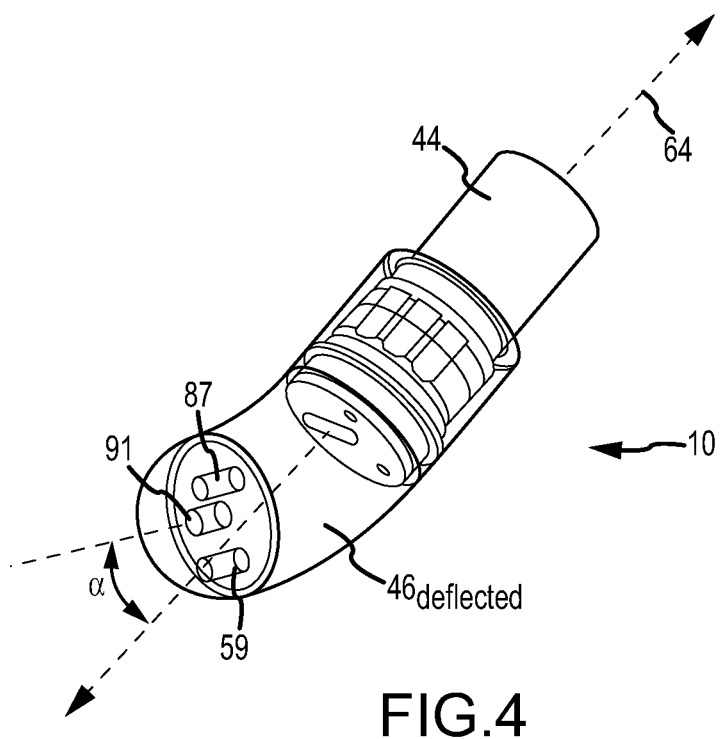
FIG. 4 is an isometric partially transparent view of the ablation electrode assembly of FIG. 2 illustrating the flexibility of the outer shell of the ablation electrode assembly of FIG. 2.

At least a portion of the thermal sensors 58 can also be routed through the electrode shell 46. At least a portion of the thermal sensors 58 can be surface mounted to an inner surface 86 of the electrode shell 46 in accordance with an embodiment of the disclosure. At least a portion of the thermal sensors 58 can be surface mounted to the inner surface 86 of the electrode shell 46 in any manner known to those of ordinary skill in the art. Referring now to FIG. 4, the electrode shell 46 can include a receptacle 59 for receiving at least a portion of the thermal sensor 58 described hereinabove which can be routed through the electrode shell 46 in accordance with an embodiment of the disclosure. For example and without limitation, the electrode shell 46 can include a tab extension (not shown) extending radially inwardly from the inner surface 86 of the electrode shell 46 having at least one receptacle through which at least a portion of the thermal sensor 58 can be routed. Although a tab extension is mentioned in detail, other structures can be utilized to provide a receptacle through which the thermal sensors 58, or any number of other components, can be routed.

Inner surface 54 of the electrode core member 44 defines an inner cavity 60 as best illustrated in FIG. 3. In an embodiment of the disclosure, the electrode core member 44 includes an irrigation passageway 62 that extends from the inner cavity 60 to the outer surface 52 of the electrode core member 44. Electrode core member 44 includes a plurality of irrigation passageways 62 in an embodiment. Each of the irrigation passageways 62 extend from the inner cavity 60 of the electrode core member 44 to the outer surface 62 of the electrode core member 44. Each of the irrigation passageways 62 can be located closer to the first end 48 of the electrode core member 44 than to the second end 50 of the electrode core member 44 in accordance with an embodiment of the disclosure. Each of the irrigation passageways 62 can generally extend radially outwardly. The ablation electrode assembly 10 can include a longitudinal axis 64. In an embodiment, each of the irrigation passageways 62 can be oriented at about 90 degrees relative to the longitudinal axis 64 of the ablation electrode assembly 10. In accordance with other embodiments, one or more of the irrigation passageways 62 can be angled generally toward the first end 48 of the electrode core member 44 at an acute angle (e.g., between about 20 to about 70 degrees, and for some embodiments, between about 30 to about 65 degrees) with respect to the longitudinal axis 64 of the ablation electrode assembly 10. The orientation of the irrigation passageways 62 vary depending on the design of the ablation electrode assembly 10. The irrigation passageways 62 of the electrode core member 44 can be straight or curved in various embodiments of the disclosure. In accordance with an embodiment of the disclosure, the irrigation passageways 62 of the electrode core member 44 can be diametrically opposed to each other around the perimeter or circumference of the electrode core member 44. Each of the irrigation passageways 62 can be generally tubular and can have a constant diameter along their length. In an embodiment, each of the irrigation passageways 62 can have a diameter ranging in size from about 0.008 inches (about 0.20 millimeters or about 1.04 F) to about 0.015 inches (about 0.38 millimeters or about 1.95 F), and for some embodiments between about 0.010 inches (about 0.25 millimeters or about 1.30 F) to about 0.012 inches (about 0.30 millimeters or about 1.56 F). Alternate configurations having various shapes and diameters, for example, along all or portions of the length of the irrigation passageways 62 can be used in various embodiments. Each of the irrigation passageways 62 can be configured to provide proximal delivery of irrigation fluid. Delivery of irrigation fluid generally reduces char, thrombus formation, and coagulum formation, thereby enabling greater energy delivery during RF ablation.

Electrode core member 44 can comprise a thermal insulator having a reduced thermal conductivity. Electrode core member 44 can be thermally nonconductive in accordance with an embodiment of the disclosure. Electrode core member 44 can comprise an electrically nonconductive material in accordance with an embodiment of the disclosure. In general, the electrode core member 44 is lower in thermal conductivity, and preferably substantially lower, than the electrode shell 46. Electrode core member 44 can comprise a reduced thermally conductive polymer in accordance with an embodiment of the disclosure. A reduced thermally conductive polymer is one with physical attributes that decrease heat transfer by about 10% or more, provided that the remaining structural components are selected with the appropriate characteristics and sensitivities desired for the ablation electrode assembly 10. One reduced thermally conductive material can include polyether ether ketone (PEEK). Additional examples of thermally nonconductive or reduced thermally conductive materials that can be useful in conjunction with the instant disclosure include, but are not limited to, high density polyethylene (HDPE), polyimide thermoplastic resins, such as those resins sold under the trademark ULTEM® and as generally available from General Electric Plastics (now known as SABIC Innovative Plastics), polyaryletherketones, polyurethane, polypropylene, oriented polypropylene, polyethylene, crystallized polyethylene terephthalate, polyethylene terephthalate, polyester, polyetherimide, acetyl, ceramics, and/or various combinations thereof. Electrode core member 44 can also comprise other plastic materials such as silicone or polyether block amides such as those sold under the trademark PEBAX® and generally available from Arkema France in other embodiments of the disclosure.

Electrode shell 46 is a relatively thin shell defining an inner volume as best illustrated in FIGS. 2-3. Electrode shell 46 is configured to improve temperature correlation between the electrode and tissue interface because it is a relatively thin shell in place of a solid mass (i.e., requiring less time for the electrode shell 46 to register an increased temperature due to the application of energy). Electrode shell 46 can be a relatively thin shell (i.e., have a small thickness) and can be external to and/or surround at least the first end 48 of the electrode core member 44. Electrode shell 46 can comprise a single layer in accordance with an embodiment of the disclosure.

At least a portion of electrode shell 46 may be generally flexible in an embodiment. For example, at least a portion of electrode shell 46 may be configured to conform to the targeted tissue 14, and may therefore, deflect and/or undergo deformation when electrode shell 46 comes into physical contact with the targeted tissue 14. In particular, the electrode shell 46 can be sufficiently flexible so that at least a distal portion of electrode shell 46 may be configured for deformation and/or deflection in a number of directions relative to the longitudinal axis 64 of ablation electrode assembly 10.

Referring now to FIG. 4, the electrode shell 46 is shown in a deflected and/or deformed position $46_{deflected}$, and is schematically shown deflected at an angle a relative to axis 64. Although this particular deflection is illustrated, electrode shell 46 may be deflected and/or deformed in various other ways, including in a direction along different axes other than the axis of the ablation electrode assembly 10. Deflection and/or deformation of the electrode shell 46 can allow the electrode shell 46 to conform to cardiac anatomy in order to improve energy efficiency during RF ablation.

Electrode shell 46 can be comprised of any electrically, and potentially thermally, conductive material known to those of ordinary skill in the art for the delivery of ablative energy to targeted tissue areas. Examples of electrically conductive materials include gold, platinum, iridium, palladium, stainless steel, and/or any combination thereof. In particular, a combination of platinum and iridium can be used in various combinations. Electrode shell 46 can be fabricated or constructed in accordance with any method or technique known to one of ordinary skill in the art. For example and without limitation, electrode shell 46 can be fabricated or constructed using so-called deep drawn metal forming techniques, metal-punching techniques, electroforming techniques (e.g., electroforming over a sacrificial form that can include rods or other internal forms that melt or are subsequently dissolved), powdered metal techniques (e.g., pressing powered metal into a slug, sintering at high heat, and then covering the pressed and sintered slug with a metallic covering member), liquid metal injection molding (MIM) techniques, and the like. The powered metal techniques can also include sacrificial members, and the pressed and sintered slug can itself conduct fluid and thermal energy inside, around, and against the metallic covering.

Figure 5A:
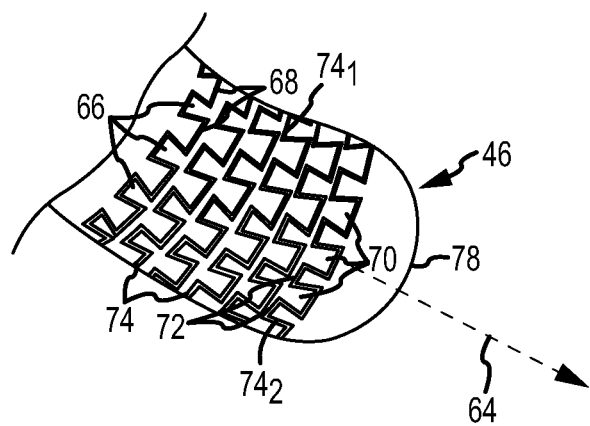
FIG. 5A is an isometric view of a portion of the outer shell of the ablation electrode assembly of FIG. 2 in accordance with a first embodiment of the invention.
Figure 5B:
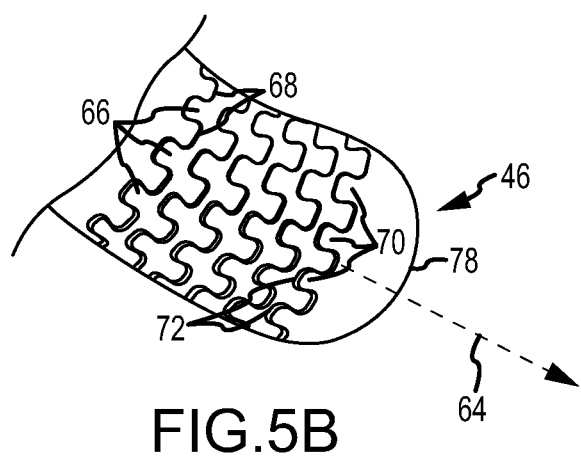
FIG. 5B is an isometric view of a portion of the outer shell of the ablation electrode assembly of FIG. 2 in accordance with a second embodiment of the invention.

Referring to FIGS. 5A-5B, in accordance with an embodiment of the disclosure wherein the electrode shell 46 comprises a metal, the electrode shell 46 is comprised of a single member that is formed into a helix, or spiral, and extends from distal end 78 to proximal end 80 or at least a portion thereof. For example and without limitation, at least a portion of the electrode shell 46 can be similar to the tip element described and illustrated in U.S. Patent Application Publication No. 2010/0174177 titled "Magnetically Guided Catheter," the entire disclosure of which is incorporated herein by reference. Referring again to FIGS. 5A-5B, at least a portion of the electrode shell 46 includes a first set of projections 66 defining at least in part a corresponding first set of recesses 68. At least a portion of the electrode shell 46 includes a second set of projections 70 defining at least in part a corresponding second set of recesses 72. The first set of projections 66 and the second set of projections 70 are alternately spaced and extend away from the electrode shell 46 in opposite directions from one another along the length of the helix or spiral. In particular, each of the first set of projections 66 extend proximally (i.e., away from the distal end 78 of the electrode shell 46), and each of the second set of projections 70 extend distally (i.e., toward the distal end 78 of the electrode shell 46). The first set of projections 66 can be staggered and/or offset from the second set of projections 70 such that the first set of projections are positioned between the second set of projections 70. The first set of recesses 68 and the second set of recesses 72 are complementary in shape to an outer contour of the first set of projections 66 and the second set of projections 70, respectively, but inversely shaped from same. In the embodiment of the disclosure illustrated in FIG. 5A, each of the first set of projections 66, the first set of recesses 68, the second set of projections 70, and the second set of recesses 72 are trapezoidal in shape. Although a trapezoidal shape is mentioned in detail, the projections 66, 70 and recesses 68, 72 can be other any number of other shapes in accordance with other embodiments of the disclosure. For example and without limitation, in the embodiment of the disclosure illustrated in FIG. 5B, each of the first set of projections 66, the first set of recesses 68, the second set of projections 70, and the second set of recesses 72 can be rounded (e.g., teardrop) in shape.

The electrode shell 46 can be fabricated such that the projections 66 from a section of the electrode shell 46 extend into, and are captured within, recesses 72 from an adjacent section of electrode shell 46 to form an interlocking arrangement. In addition, projections 70 from a section of the electrode shell 46 extend into, and are captured within, recesses 68 from an adjacent section of electrode shell 46 to form an interlocking arrangement. Accordingly, at least one of the first set of projections 66 is configured to interlock with at least one of the second set of recesses 72, and at least one of the second set of projections 70 is configured to interlock with at least one of the first set of recesses 68. Due to projections 66, 70 being complementary in shape to recesses 72, 68, respectively, and thus defining sockets or compartments for projections 66, 70, projections 66, 70 are moveable only a defined distance within recesses 72, 68. In particular, electrode shell 46 is positionable to create a space or gap 74 between leading edges of projections 66, 70 and inner edges or recesses 72, 68, respectively. Projections 66, 70 and recesses 68, 72 of the electrode shell 46 extend along at least more than half the length of electrode shell 46. For example and without limitation, projections 66, 70 and recesses 68, 72 extend along at least two thirds of the length of the electrode shell 46. Although these lengths are mentioned in detail, projections 66, 70 and recesses 68, 72 can extend for more or less of the entire length of the electrode shell 46 in accordance with various embodiments of the disclosure. For example and without limitation, the projections 66, 70 and recesses 68, 72 can be uniformly spaced along the length of the electrode shell 46 and can also be uniformly spaced around the perimeter (e.g., circumference) of the electrode shell 46. Although uniform spacing is mentioned in detail, projections 66, 70 and recesses 68, 72 can be differently spaced along the length and/or perimeter of the electrode shell 46 in accordance with various embodiments of the disclosure. For example and without limitation, the projections 66, 70 and recesses 68, 72 can be uniformly sized along the length of the electrode shell 46 and can be uniformly sized around the perimeter (e.g., circumference) of the electrode shell 46. Although uniform sizing is mentioned in detail, projections 66, 70 and recesses 68, 72 can be differently sized along the length and/or perimeter of the electrode shell 46 in accordance with various embodiments of the disclosure.

As a consequence of gaps 74, and also the complementary shape of projections 66, 70 and recesses 68, 72, projections 66, 70 are provided a freedom of movement within recesses 68, 72 without being able to be removed therefrom. Accordingly, sections of electrode shell 46 can move toward and away from each other a defined distance to decrease and increase, respectively, gaps 74. The ability of sections of electrode shell 46 to move toward and away from each other a defined distance to decrease and increase, respectively, gaps 74 can constrain the flexure of the electrode shell 46 and limit the range of extensibility of the electrode shell 46.

It is possible for sections of electrode shell 46 to move relative to one another in multiple ways. For example, the electrode shell 46 can be compressed so that all of gaps 74 are closed, or nearly closed, to reduce the longitudinal length of the electrode shell 46 by the cumulative dimensions of gaps 74 along a longitudinal axis 64. Additionally, sections of electrode shell 46 can exhibit cascaded and/or sequential movement along longitudinal axis 64 wherein some gaps 74 are closed along longitudinal axis 64 while other gaps remain open, either partially or fully. This allows gaps 74 between any adjacent sections of the electrode shell 46 to be opened or closed in an uneven or non-uniform manner. As such, gaps $74_1$ on a first portion of the perimeter (e.g., circumference) of the electrode shell 46 may be closed while gaps $74_2$ on another second portion (e.g., opposing the first portion) of the electrode shell may be opened. The result of such a configuration is that the electrode shell 46 curves in the direction of the closed gaps $74_1$ and away from the direction of the opened gaps $74_2$. It can be appreciated that movement in vertical and horizontal planes can simultaneously occur due to the interlocking construction of electrode shell 46 to flex and deflect at least the distal end 78 of the electrode shell 46 to a practically unlimited number of positions. At least a portion of the electrode shell 46 can deflect in the manner described due to, for example and without limitation, impact forces on an outer surface 84 of the electrode shell 46 in use. The projections 66, 70 and recesses 68, 72 can be configured to allow the electrode shell 46 to have sufficient flexibility for deformation and/or deflection of at least a portion of the electrode shell 46 for allowing the electrode shell 46 to conform to cardiac anatomy in order to improve energy efficiency of the delivery of ablation energy. This is because the flexible electrode shell 46 can engage a larger surface area upon contact with targeted tissue 14, thereby improving contact stability and optimizing energy transfer to the targeted tissue 14 while reducing catheter induced mechanical stress.

The interlocking projections 66, 70 and recesses 68, 72 can be fabricated and/or generated by laser-cutting techniques known to those of ordinary skill in the art. For example and without limitation, electrode shell 46 is laser cut from a material suitable for surgical use, such as an electrically conductive, non-corrosive material. As described hereinabove, examples of suitable materials include gold, platinum, iridium, palladium, stainless steel, and/or any combination thereof. Projections 66, 70 and recesses 68, 72 can be laser cut out of a cylindrical piece of material. As the number of helices increases in electrode shell 46, the flexing capability of the electrode shell 46 also increases. In addition, as the pitch of the helix (i.e., the distance along the axis of the helix corresponding to one turn) decreases, the ability of the electrode shell 46 to move relative to itself increases. The flexibility can be further adjusted by providing different numbers and shapes of projections 66, 70 and recesses 68, 72 to produce an electrode shell 46 that flexes to varying degrees to meet different objective. For example and without limitation, RF energy can be more specifically targeted to desired tissue areas for ablation procedures when electrode shell 46 is flexed than when it is not flexed and can provide physicians with additional positioning capability.

In accordance with another embodiment of the disclosure where the electrode shell 46 comprises a metal, the electrode shell 46 may not include interlocking projections 66, 70 and recesses 68, 72, but can instead comprise wound and/or braided metallic wires. The spacing and/or the configuration of wires, including the distance between adjacent turns of the wire can vary in accordance with various embodiments of the disclosure.

In accordance with another embodiment of the disclosure, the electrode shell 46 can comprise a polymer material. In particular, the electrode shell 46 can comprise an electrically conductive polymer. The polymer can comprise a silicone material, for example. The polymer can have electrically conductive particles dispersed therein at a predefined density in accordance with an embodiment of the disclosure. The density of the electrically conductive particles can be defined to achieve a desired electrical conductivity. The electrically conductive particles can comprise metal particles in an embodiment. For example and without limitation, the electrically conductive particles can comprise a metal such as gold, silver, platinum, iridium, titanium, tungsten, or a combination thereof. The polymer material of the electrode shell 46 can be the same as the polymer material described and illustrated in U.S. Patent Application Publication No. 2009/0171188 titled "Flexible Polymer Electrode for MRI-Guided Positioning and Radio Frequency Ablation," the entire disclosure of which is incorporated herein by reference.

Referring back to FIGS. 2-3 in particular, electrode shell 46 has a first end 78 and a second end 80. The first end 78 can be a distal end, and the second end 80 can be a proximal end in accordance with an embodiment of the disclosure. Electrode shell 46 can be generally cylindrical in shape. The first end 78 of the electrode shell 46 can be partially spherical or generally hemispherical in shape in accordance with an embodiment of the disclosure. The second end 80 of the electrode shell 46 can be configured for mechanical connection to the electrode core member 44. For example and without limitation, the second end 80 of the electrode shell 46 can be configured for mechanical connection to the first end 48 of the electrode core member 44. Electrode shell 46 can be coupled together or connected with electrode core member 44 along the same longitudinal axis 64. Electrode core member 44 and electrode shell 46 can be mechanically connected or coupled together by any known mechanisms including, for example and without limitation, adhesive bonding, press-fit configurations, snap-fit configurations, ultrasonic staking, mechanical deformation, or any other mechanism known to one of ordinary skill in the art. In an embodiment, the electrode shell 46 can be configured for mechanical connection to the first end 48 of the electrode core member 44. The first end 48 of the electrode core member 44 can have an outer diameter that is substantially equal to the inner diameter of the electrode shell 46 at the second end 80 of the electrode shell 46. The electrode core member 44 can also include a radially outwardly extending flange 82 near the first end 48 of the electrode core member 44. The radially outwardly extending flange 82 has an outer diameter that is substantially equal to the outer diameter of the proximal end 80 of the electrode shell 46.

The electrode shell 46 also has an outer surface 84 and inner surface 86 as best illustrated in FIG. 3. In an embodiment, at least one retaining wire and/or safety wire (not shown) can be extended through a lumen in the catheter shaft 18 and can be connected to the ablation electrode assembly 10. The retaining wire and/or safety wire can comprise a high tensile strength liquid crystal polymer (LCP) fiber wire in accordance with an embodiment of the disclosure. The retaining wire and/or safety wire can be configured to ensure that that the ablation electrode assembly 10 is not separated from the catheter shaft 18 to which it is attached during movement of the irrigated catheter assembly within a body 20. One end of the retaining wire and/or safety wire can be affixed in the catheter 16, for example, using an anchor pin. An opposing end of the retaining wire and/or safety wire can be affixed to the electrode shell 46. In particular, at least a portion of the retaining wire and/or safety wire can be routed through the electrode shell 46. At least a portion of the retaining wire and/or safety wire can be surface mounted to the inner surface 86 of the electrode shell 46 in accordance with an embodiment of the disclosure. At least a portion of the retaining wire and/or safety wire can be surface mounted to the inner surface 86 of the electrode shell 46 in any manner known to those of ordinary skill in the art. Referring now to FIG. 4, the electrode shell 46 can include a receptacle 87 for receiving at least a portion of the retaining wire and/or safety wire described hereinabove which can be routed through the electrode shell 46 in accordance with an embodiment of the disclosure. For example and without limitation, the electrode shell 46 can include a tab extension (not shown) extending radially inwardly from the inner surface 86 of the electrode shell 46 having at least one receptacle through which at least a portion of the retaining wire and/or safety wire can be routed and affixed to the electrode shell 46. Although a tab extension is mentioned in detail, other structures can be utilized to provide a receptacle through which the thermal sensors 58, or any number of other components, can be routed. The retaining wire and/or safety wire can be affixed to the electrode shell 46 by tying a knot in the end of the retaining wire and/or safety wire and press-fitting the knotted end into a receptacle 87. Adhesive can then be applied to bond the knot and the retaining wire and/or safety wire into the receptacle 87.

In accordance with an embodiment of the disclosure, a plug and/or bladder 88 can be configured to fill the inner volume defined by the electrode shell 46. The plug and/or bladder 88 can also provide stability for the electrode shell 46 and maintain some degree of resistance to deflection (i.e., a recovery force) in some embodiments of the disclosure. The plug and/or bladder 88 is best illustrated in FIG. 3. The plug and/or bladder 88 can comprise a polymer in accordance with an embodiment of the disclosure. For example and without limitation, the polymer can comprise silicone. The plug and/or bladder 88 can be relatively soft in accordance with an embodiment of the disclosure. For example and without limitation, the durometer of the plug and/or bladder 88 can be modified and/or adjusted to provide varying degrees of flexibility based on the desired characteristics of the end user of the ablation electrode assembly 10. In other words, the plug and/or bladder 88 can have a predefined durometer to achieve a desired flexibility. The plug and/or bladder 88 can be configured to prevent ingress of blood and/or fluids into the volume defined by the electrode shell 46. The electrode shell 46 and plug and/or bladder 88 can be immediately and/or directly adjacent to each other in an embodiment of the disclosure. The electrode shell 46 and plug and/or bladder 88 can define a space therebetween in accordance with other embodiments of the disclosure. The configuration of the space can vary greatly and can be regular or irregular and can include support members (e.g., flutes, bosses, posts, and the like) to maintain separation between the electrode shell 46 and the plug and/or bladder 88 in some embodiments of the disclosure. The space can be configured as an annular space in accordance with an embodiment of the disclosure.

Electrode shell 46 can be electrically connected to an ablation system 42 to allow for the delivery of ablative energy, or the like. Electrode shell 46 can be electrically connected to an ablation system 42 in any manner conventional in the art. For example, a power wire 90 (best illustrated in FIGS. 2-3) can be provided within electrode core member 44 and electrode shell 46 of ablation electrode assembly 10. The power wire 90 can extend through a lumen(s) provided within the ablation electrode assembly 10. At least a portion of the power wire 90 can be surface mounted to the inner surface 86 of the electrode shell 46 in accordance with an embodiment of the disclosure. At least a portion of the power wire 90 can be surface mounted to the inner surface 86 of the electrode shell 46 in any manner known to those of ordinary skill in the art. Referring again to FIG. 4, the electrode shell 46 can include a receptacle 91 for receiving at least a portion of the power wire 90 described hereinabove which can be routed through the electrode shell 46 in accordance with an embodiment of the disclosure. For example and without limitation, the electrode shell 46 can include a tab extension (not shown) extending radially inwardly from the inner surface 86 of the electrode shell 46 through which at least a portion of the power wire 90 can be routed. Although a tab extension is mentioned in detail, other structures can be utilized to provide a receptacle through which the power wire 90, or any number of other components, can be routed.

Referring back to FIG. 1, the ablation system 42 can be comprised of, for example, an ablation generator 92 and one or more ablation patch electrodes 94. The ablation generator 92 generates, delivers, and controls ablation energy (e.g., RF) output by the irrigated catheter assembly and the electrode shell 46 of the ablation electrode assembly 10 thereof, in particular. The generator 92 can be conventional in the art and can comprise a commercially available unit sold under the model number IBI-1500T RF Cardiac Ablation Generator, available from St. Jude Medical, Inc. In an exemplary embodiment, the generator 92 can include an RF ablation signal source 96 configured to generate an ablation signal that is output across a pair of source connectors: a positive polarity connector SOURCE (+), which electrically connects to the electrode shell 46 of the ablation electrode assembly 10 of the irrigated catheter assembly; and a negative polarity connector SOURCE (−), can be electrically connected to one or more of the patch electrodes 94. It should be understood that the term connectors as used herein does not imply a particular type of physical interface mechanism, but is rather broadly contemplated to represent one or more electrical nodes (including multiplexed and de-multiplexed nodes). The source is configured to generate a signal at a predetermined frequency in accordance with one or more user specified control parameters (e.g., power, time, etc.) and under the control of various feedback sensing and control circuitry. The source can generate a signal, for example, with a frequency of about 450 kHz or greater for RF energy. The generator 92 can also monitor various parameters associated with the ablation procedure including, for example, impedance, the temperature at the distal tip of the irrigated catheter assembly, applied ablation energy, power, force, proximity, and the position of the irrigated catheter assembly, and provide feedback to the clinician or another component within the irrigated catheter assembly regarding these parameters.

Still referring to FIG. 1, the ablation system 42 can further include a control system 98. The control system 98 is configured to determine the temperature of the targeted tissue 14 (i.e., the tissue to be ablated) and/or an appropriate ablation technique. The electrode shell 46 of the ablation electrode assembly 10 can be connected to the control system 98 with wires. The ablation generator 92 can form part of the control system 98 in accordance with some embodiments or can be separate from the control system 98 in other embodiments. The thermal sensors 58 can be connected to the control system 98. For example and without limitation, wires can extend through lumens in the catheter. Devices for determining pressure, temperature, and a flow parameter of a flowing fluid available from Radi Medical Systems AB, and as generally shown with reference to at least U.S. Pat. No. RE39,863 entitled "Combined flow, pressure and temperature sensor," the entire disclosure of which is incorporated herein by reference can be used to monitor and/or control the quantity of flow of irrigation fluid within or from the catheter at one or more locations using a flow-from pressure algorithm as described therein or as known to those of ordinary skill in the art. These devices for determining pressure, temperature, and a flow parameter of a flowing fluid can also be connected to the control system 98. The energy provided to the ablation electrode assembly 10 can be increased by the control system 98 by increasing the power and/or length of energy delivery (e.g., amplitude and/or operating time) during the ablation cycle. The energy provided to the ablation electrode assembly 10 can be decreased by decreasing the power and/or length of time of energy delivery (e.g., frequency and/or operating time) during the ablation cycle. The ablation technique that is selected by the control system 98 can be selected to produce a certain, predetermined temperature in the targeted tissue 14 that will form a desired lesion in the targeted tissue 14. While the desired lesion can be transmural in some embodiments, the characteristics of the desired lesion can vary significantly. The certain, predetermined temperature in the targeted tissue 14 that will form a desired lesion in the targeted tissue 14 can be affected by the thermal response of the targeted tissue. The thermal response of the targeted tissue 14 can be affected by a number of variables including tissue thickness, amount of fat and muscle, blood flow through the region, and blood flow at the interface of the ablation electrode assembly 10 and the targeted tissue 14.

Referring back to FIGS. 2-4, in accordance with an embodiment of the disclosure, the ablation electrode assembly 10 further includes an irrigant distribution element 100. Irrigant distribution element 100 can be configured as a generally annular ring in accordance with an embodiment of the disclosure. The irrigant distribution element 100 has a first end 102 and a second end 104. The first end 102 can be a proximal end, and the second end 104 can be a distal end in accordance with an embodiment of the disclosure. At least a portion of the first end 102 of the irrigant distribution element 100 can engage a catheter shaft 18 in which the electrode core member 44 can be located. At least a portion of the second end 104 of the irrigant distribution element 100 can surround and/or encircle at least a portion of the electrode core member 44 and further, can define a circumferential irrigation port 106 between the irrigant distribution element 100 and the electrode core member 44 in accordance with an embodiment of the disclosure.

Irrigant distribution element 100 is configured to guide irrigation fluid toward electrode shell 46 about and along outer surface 84 of the electrode shell 46, and in particular, direct the fluid (e.g., irrigant) flow in a direction substantially parallel with the outer surface 84 of the electrode shell 46. Irrigant distribution element 100 can include a fluid shaping member 108 that helps ensure that the fluid flow tends toward the surface 84 of the electrode shell 46 of the ablation electrode assembly 10. For example and without limitation, the fluid shaping member 108 of the irrigant distribution element 100 can include a channel, rifling, boss, hump, chamfer, and/or combination thereof on a surface of the irrigant distribution element 100 defining the circumferential irrigation port 106. The fluid shaping member 108 is configured to disturb fluid flow (e.g., cause fluid flowing closer to the outer surface 52 of the electrode core member 44 to slow down relative to fluid flowing farther from the outer surface 52 of the electrode core member 44), thereby helping to ensure that the fluid flow tends toward the surface 84 of the electrode shell 46. In this way, the flow of irrigant can be turbulent in order to provide an enveloping flow pattern adjacent to the outer surface 84 of the electrode shell 46 of the ablation electrode assembly 10 for mixing with, displacing, and/or diluting blood that can be in contact with the ablation electrode assembly 10 in order to help prevent stasis and the formation of coagulum. Although flexing of the electrode shell 46 can affect the flow of irrigant, it is expected that the flexing of the electrode shell 46 will not have a significant clinical impact since any flexing and/or deflection of the electrode shell 46 is limited and relatively small in accordance with an embodiment of the disclosure.

The configuration of irrigant distribution element 100 can improve fluid flow of the irrigation fluid such that the total flow rate (or volume delivered per unit of time) of irrigation fluid can be exceedingly low as compared to traditional irrigation flow rates (and volumes). In other words, overall total fluid volumes of irrigation fluid can be much lower than the prior art or than those fluid volumes typically utilized in clinical practice, which can be especially valuable for patients already suffering from fluid overload (e.g., patient having heart failure and the like). Overall total fluid volume can range from low single digits to about ten or so milliliters per minute while effectively reducing or eliminating char and coagulum and improving temperature correlation for precise control of power to maintain a temperature during ablation procedures.

Valve members, for example and without limitation, such as those shown and described in co-owned U.S. Patent Application Publication No. 2008/0161795 entitled "Irrigated Ablation Catheter System With Pulsatile Flow To Prevent Thrombus," the entire disclosure of which is incorporated herein by reference, or other similar flow control features can be used in connection with catheters incorporating ablation electrode assembly 10 in order to change the flow rate of irrigation fluid. In other embodiments, the flow control features can be part of an ancillary control system separate from and to be used in conjunction with catheters. The valves can operate automatically without user input and/or can operate based on feedback recorded during RF ablation by the ECU of the visualization, navigation, and/or mapping system 30. The feedback can relate to time, temperature, and/or impedance, for example and without limitation. Circuitry for implementing the feedback automatically in a control algorithm can be readily provided by those having ordinary skill in the art after becoming familiar with the teachings herein.

Figure 6:
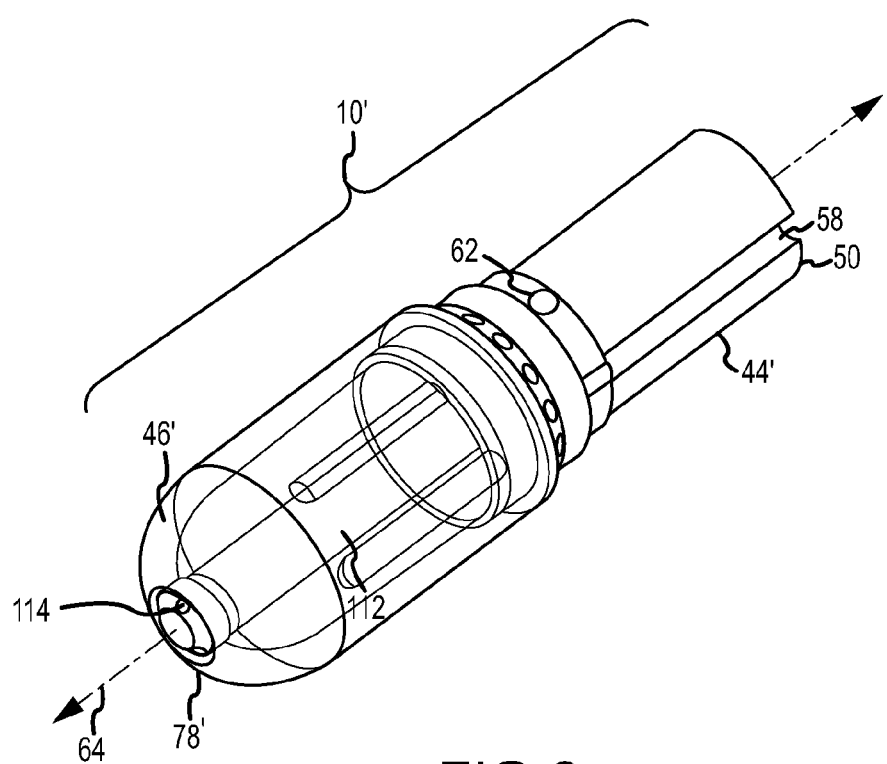
FIG. 6 is an isometric partially transparent view of an ablation electrode assembly in accordance with a second embodiment of the disclosure.
Figure 7:
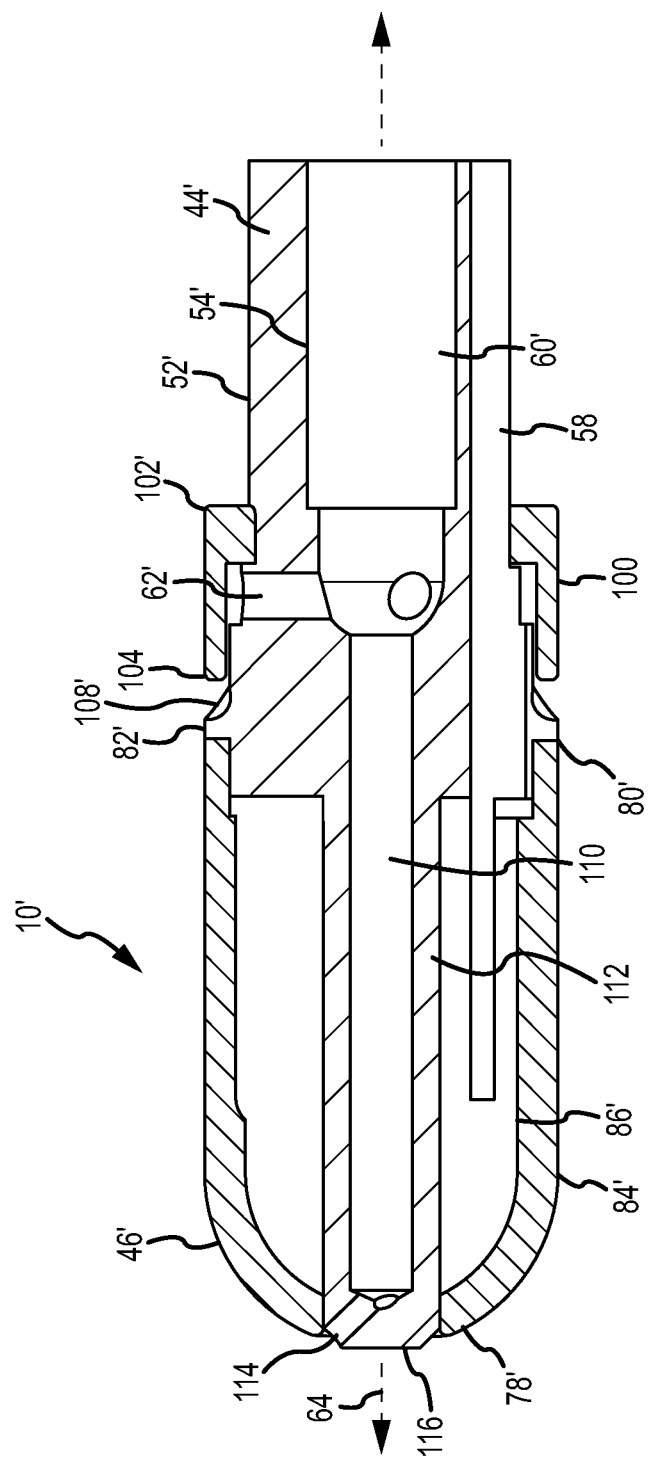
FIG. 7 is a cross-sectional view of the ablation electrode assembly of FIG. 6.

Referring now to FIGS. 6-7, ablation electrode assembly 10' can include an electrode core member 44' and an electrode shell 46' in accordance with a second embodiment of the invention. The ablation electrode assembly 10' in accordance with a second embodiment of the disclosure can be substantially identical to the ablation electrode assembly 10 as described hereinabove including the electrode shell 46' being generally flexible in an embodiment (e.g., configured to conform to the targeted tissue 14 by deflection and/or deformation when the electrode shell 46' comes into physical contact with the targeted tissue 14), except that the electrode core member 44' and/or the electrode shell 46' can be modified to provide distal delivery of irrigation fluid in which at least a portion of the irrigation fluid is transferred to a distal exhaust port. The ablation electrode assembly 10' that is configured to provide both proximal and distal delivery of irrigation fluid can be especially beneficial to reduce thrombus formation and/or charring at the distal end (e.g., tip) of the ablation electrode assembly 10'. By providing both proximal and distal delivery of irrigation fluid, it can further displace blood and prevent stasis in the areas adjacent the electrode shell 46' of the ablation electrode assembly 10'.

Still referring to FIGS. 6-7, ablation electrode assembly 10' is configured for distal delivery of irrigation fluid with an axially extending passageway 110 extending from the inner cavity 60' of the electrode core member 44' toward the first end 78' of the electrode shell 46'. The axially extending passageway 110 can be defined by a generally cylindrical member 112. The generally cylindrical member 112 can be integral with the inner core member 44' in accordance with various embodiments of the disclosure. The generally cylindrical member 112 can also be separate from the inner core member 44' in accordance with various other embodiments of the disclosure. For example and without limitation, the generally cylindrical member 112 may comprise a close wound coil spring with a liner or jacket of low durometer polymer. For another example, the generally cylindrical member 112 may comprise a polymer tube. The cylindrical member 112 can be sufficiently flexible so that at least a portion of the cylindrical member 112 may be configured for deformation and/or deflection in a number of directions relative to the longitudinal axis 64 of ablation electrode assembly 10. Although the member 112 is defined as generally cylindrical, the member 112 can comprise any number of various shapes in accordance with embodiments of the disclosure. In accordance with another embodiment of the disclosure, the axially extending passageway 110 can be defined by a through-hole disposed in the plug and/or bladder 88 configured to fill the inner volume defined by the electrode shell 46. As described hereinabove, the plug and/or bladder 88 can comprise silicone in accordance with an embodiment of the invention. The total range of deflection of cylindrical member 112 and/or the plug and/or bladder 88 can be relatively small such that stress on the conduit is not expected to adversely affect the function of the ablation electrode assembly 10'.

In accordance with one embodiment of the disclosure, the axially extending passageway 110 can extend to the distal end 78' of the electrode shell 46'. In accordance with another embodiment of the disclosure as generally illustrated in FIGS. 6-7, the axially extending passageway 110 can transition into one or more ports 114 near the distal end 116 of the member 112. Port(s) 114 can be configured to enable irrigation fluid flowing through the axially extending passageway 110 to flow to a first end 78' of the electrode shell 46', therein substantially irrigating the first end 78' (e.g., tip) of electrode shell 46' of the ablation electrode assembly 10'. For example and without limitation, the member 112 can include three ports 114. Each of the port(s) 114 can be oriented at a generally acute angle (e.g., about 45 degrees) relative to the longitudinal axis 64 of the ablation electrode assembly 10'. The orientation of the port(s) 114 varies depending on the design of the ablation electrode assembly 10'. The port(s) 114 can be substantially equally spaced around the circumference of the member 112 in an embodiment of the disclosure. The port(s) 114 are configured to extend from the distal end of the axially extending passageway 110 to the distal end 78' of the electrode shell 46'.

In an embodiment of the disclosure, a coating (not shown) can be disposed on at least a portion of the member 112 that defines the axially extending passageway 100. For example and without limitation, a coating can be especially useful if the member 112 is not integral with the inner core member 44' and instead comprises a material that may be electrically conductive. The coating can be comprised of an electrically non-conductive material. For example and without limitation, the coating can be comprised of diamond, diamond-like carbon (DLC), or polytetrafluoroethylene (PTFE), which is commonly sold by the E. I. du Pont de Nemours and Company under the trademark TEFLON®. In an embodiment of the disclosure, the coating can be provided around the entire circumference and along the entire length of the axially extending passageway 110. However, the coating can be provided only around a portion of the circumference and/or only along a portion of the length of the axially extending passageway 110 in accordance with various embodiments of the disclosure. The amount of the coating provided around the circumference and/or length of the axially extending passageway 110 or portion thereof can vary depending on the relative requirements of ablation electrode assembly 10'.

Although ablation electrode assemblies 10, 10' are described and illustrated with a single electrode core member 44, 44' and a single electrode shell 46, 46', an ablation catheter 16 can include two or more electrode core members 44, 44' and/or two or more electrode shells 46, 46' in accordance with various embodiments of the disclosure. Furthermore, although ablation electrode assemblies 10, 10' are described and illustrated such that the electrode shell 46, 46' is located distally of the electrode core member 44, 44', at least one electrode shell 46, 46' can be located proximally of an electrode core member 44, 44' in accordance with various embodiments of the disclosure.

Figure 8:
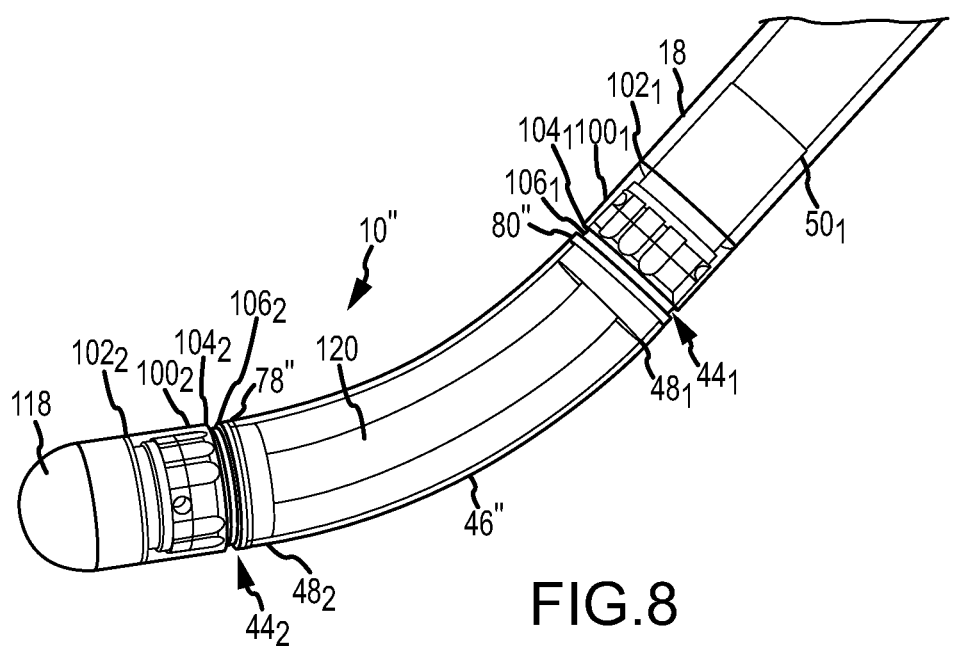
FIG. 8 is an isometric partially transparent view of an ablation electrode assembly in accordance with a third embodiment of the disclosure.

For example and without limitation, an ablation electrode assembly 10" can include two or more electrode core members 44$_1$, 44$_2$ and a single electrode shell 46" as generally illustrated in FIG. 8. The first electrode core member 44$_1$ can be disposed proximally relative to the electrode shell 46. The first electrode core member 44$_1$ can be substantially identical to the electrode core member 44, 44' described hereinabove. The second electrode core member 44$_2$ can be disposed distally relative to the electrode shell 46. The second electrode core member 44$_2$ can be substantially identical to the electrode core member 44, 44' described hereinabove; however, the second electrode core member 44$_2$ can be oriented such that the first and second electrode core members 44$_1$, 44$_2$ face in opposing directions. Accordingly, the first end 48$_2$ of the second electrode core member 44$_2$ can be a proximal end, and the second end (not shown) of the second electrode core member 44$_2$ can be a distal end. Electrode shell 46" can be substantially identical to the electrode shell 46 described herein above. Electrode shell 46" can be generally cylindrical in shape, and both the first and second ends 78", 80" of the electrode shell 46" can be open. In particular, the first end 78" of the electrode shell 46" can be configured for connection to the second electrode core member 44$_2$ that is located distally of the electrode shell 46", and the second end 78" of the electrode shell 46" can be configured for connection to the first electrode core member 44$_1$ that is located proximally of the electrode shell 46".

The ablation electrode assembly 10" generally illustrated in FIG. 8 can also include two or more irrigant distribution elements 100$_1$, 100$_2$. Irrigant distribution elements 100$_1$, 100$_2$ can be substantially identical to the irrigant distribution element 100 described hereinabove. At least a portion of the first end 102$_1$ of the first irrigant distribution element 100$_1$ can engage a catheter shaft 18 in which the first electrode core member 44$_1$ can be located. At least a portion of the second end 104$_1$ of the first irrigant distribution element 100$_1$ can surround and/or encircle the first electrode core member 44$_1$ and further, can define a circumferential irrigation port 106$_1$ between the first irrigant distribution element 100$_1$ and the electrode core member 44$_1$. The circumferential irrigation port 106$_1$ is configured to guide irrigation fluid toward electrode shell 46", and therefore, directs the irrigation fluid distally. At least a portion of the first end 102$_2$ of the second irrigant distribution element 100$_2$ can engage a tip electrode 118. The tip electrode 118 may or may not be flexible in accordance with various embodiments of the disclosure. At least a portion of the second end 104$_2$ of the second irrigant distribution element 100$_2$ can surround and/or encircle the second electrode core member 44$_2$, and further, can define a circumferential irrigation port 106$_2$ between the second irrigant distribution element 100$_2$ and the second electrode core member 44$_2$. The circumferential irrigation port 106$_2$ is configured to guide irrigation fluid toward electrode shell 46", and therefore, directs the irrigation fluid proximally. An irrigant supply line 120 can be disposed between the first electrode core member 44$_1$ and the second electrode core member 44$_2$. The irrigant supply line 120 can be the same as or can be in fluid communication with the fluid delivery tube 22 disposed within the catheter shaft 18.

Figure 9:
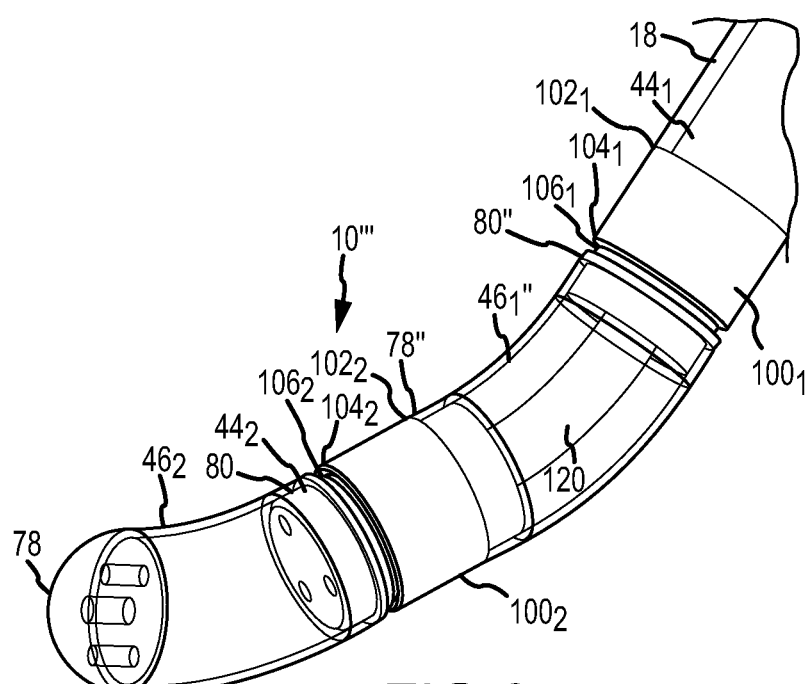
FIG. 9 is an isometric partially transparent view of an ablation electrode assembly in accordance with a fourth embodiment of the disclosure.

Referring now to FIG. 9, ablation electrode assembly 10''' can include two or more electrode core members 44$_1$, 44$_2$ and two or more electrode shells 46"$_1$, 46$_2$. Although two electrode core members 44$_1$, 44$_2$ and two electrode shells 46"$_1$, 46$_2$ are generally illustrated, the ablation electrode assembly 10''' can include any number of electrode core members 44 and electrode shells 46 in accordance with various embodiments of the disclosure. The first electrode core member 44$_1$ can be disposed proximally relative to the first electrode shell 46"$_1$. The first electrode core member 44$_1$ can be substantially identical to the electrode core member 44, 44' described hereinabove. In addition, the first electrode shell 46"$_1$ can be substantially identical to the electrode shell 46 described hereinabove. The first electrode shell 46"$_1$ can be generally cylindrical in shape, and both the first and second ends 78", 80" of the first electrode shell 46"$_1$ can be open. In particular, the first end 78" of the first electrode shell 46"$_1$ can be configured for connection to the second electrode core member 44$_2$ that is located distally of the first electrode shell 46"$_1$, and the second end 80" of the electrode shell 46"$_1$ can be configured for connection to the first electrode core member 44$_1$ that is located proximally of the first electrode shell 46".

The second electrode core member 44$_2$ can be disposed proximally relative to the second electrode shell 46$_2$. The second electrode core member 44$_2$ can be substantially identical to the electrode core member 44, 44' described hereinabove. The second electrode shell 46$_2$ can also be generally cylindrical in shape. First end 78 of the second electrode shell 46$_2$ can be closed and can be hemispherical and/or spherical in shape. The first end 78 of the second electrode shell 46$_2$ can be hemispherical and/or spherical in shape when the second electrode shell 46$_2$ is disposed at the distal tip of the ablation electrode assembly 10'''. However, the second electrode shell 46$_2$ does not have to be disposed at the distal tip of the ablation electrode assembly. Accordingly, in other embodiments of the disclosure, the second electrode shell 46$_2$ can be disposed at any location along the ablation catheter 16. Depending upon the location of the second electrode shell 46$_2$, the first end 78 of the second electrode shell 46$_2$ can be open or closed. The second end 80 of the second electrode shell 46$_2$ can be open and can be configured for connection to the second electrode core member 44$_2$.

In some embodiments, the ablation electrode assembly 10''' generally illustrated in FIG. 9 can include two or more irrigant distribution elements 100$_1$, 100$_2$. Irrigant distribution elements 100$_1$, 100$_2$ can be substantially identical to the irrigant distribution element 100 described hereinabove. At least a portion of the second end 104$_1$, 104$_2$ of each irrigant distribution element 100$_1$, 100$_2$ can surround and/or encircle each corresponding electrode core member 44$_1$, 44$_2$, and further can define a circumferential irrigation port 106$_1$, 106$_2$ between the irrigant distribution element 100$_1$, 100$_2$ and the electrode core member 44$_1$, 44$_2$. Each circumferential irrigation port 106$_1$, 106$_2$ is configured to guide irrigation fluid toward electrode shell 46"$_1$, 46$_2$, and therefore, each irrigant distribution elements 100$_1$, 100$_2$ directs the irrigation fluid distally. An irrigant supply line 120 can be disposed between the first electrode core member 44$_1$ and the second electrode core member 44$_2$. The irrigant supply line 120 can be in fluid communication with the fluid delivery tube 22 disposed within the catheter shaft 18. In accordance with various embodiments of the invention (and as generally illustrated in FIGS. 8-9), ablation electrode assemblies can include a series of two or more active ablation electrodes each with its own dependent (e.g., common source) or independent (e.g., discrete source) irrigant distribution configuration.

Although at least four embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

What is claimed is:

1. An ablation electrode assembly having a longitudinal axis, the assembly comprising:
    an electrode core member comprising a thermal insulator having a reduced thermal conductivity, the electrode core member having:
        a first end;
        a second end; and
        at least one irrigation passageway;
    an electrode shell comprising an electrically conductive material, the electrode shell defining an inner volume and the electrode shell having:
        a first end; and
        a second end, wherein the second end of the electrode shell is configured for connection to the first end of the electrode core member and wherein the electrode shell is sufficiently flexible for deflection of at least a portion of the electrode shell relative to the longitudinal axis of the ablation electrode assembly;
    an irrigant distribution element surrounding a portion of the electrode core member, the irrigant distribution element having:
        an irrigant distribution element outer surface;
        a first end; and
        a second end,
        wherein the second end of the irrigant distribution element defines a circumferential irrigation port disposed at the irrigant distribution element outer surface between the irrigant distribution element and the electrode core member.

2. The ablation electrode assembly of claim 1, wherein the electrode core member further comprises:
    an outer surface; and
    an inner surface defining an inner cavity, wherein the at least one irrigation passageway extends from the inner cavity to the outer surface of the electrode core member.

3. The ablation electrode assembly of claim 2, wherein the electrode core member further comprises an axially extending passageway extending from the inner cavity of the electrode core member toward the first end of the electrode shell.

4. The ablation electrode assembly of claim 3, further comprising at least one port extending from the axially extending passageway to the first end of the electrode shell, wherein the port is oriented at an acute angle relative to the longitudinal axis of the ablation electrode assembly.

5. The ablation electrode assembly of claim 3, wherein at least a portion of a circumference and at least a portion of the length of the axially extending passageway includes a coating of an electrically non-conductive material.

6. The ablation electrode assembly of claim 1, wherein at least a portion of the electrode shell includes a first set of projections defining at least in part a corresponding first set of recesses and wherein at least a portion of the electrode shell includes a second set of projections defining at least in part a corresponding second set of recesses, wherein at least one of the first set of projections is configured to interlock with at least one of the second set of recesses, and wherein at least one of the second set of projections is configured to interlock with at least one of the first set of recesses.

7. The ablation electrode assembly of claim 6, wherein each of the first set of projections and each of the second set of projections are trapezoidal in shape.

8. The ablation electrode assembly of claim 6, wherein each of the first set of projections and each of the second set of projections are rounded in shape.

9. The ablation electrode assembly of claim 1, wherein the electrode shell comprises braided metallic wires.

10. The ablation electrode assembly of claim 1, wherein the electrode shell comprises wound metallic wires.

11. The ablation electrode assembly of claim 1, wherein the electrode shell comprises a polymer.

12. The ablation electrode assembly of claim 11, wherein the electrode shell comprises silicone material.

13. The ablation electrode assembly of claim 11, wherein the polymer has electrically conductive particles dispersed therein at a predefined density to achieve a desired electrical conductivity.

14. The ablation electrode assembly of claim 13, wherein the particles comprise gold, silver, platinum, iridium, titanium, tungsten, or a combination thereof.

15. The ablation electrode assembly of claim 1, further comprising a plug disposed within the inner volume defined by the electrode shell.

16. The ablation electrode assembly of claim 15, wherein the plug comprises a polymer.

17. The ablation electrode assembly of claim 16, wherein the plug comprises a silicone material.

18. The ablation electrode assembly of claim 16, wherein the plug has a predefined durometer to achieve a desired flexibility.

19. The ablation electrode assembly of claim 1, wherein the irrigant distribution element is an annular ring.

20. The ablation electrode assembly of claim 1, wherein the irrigant distribution element further comprises a fluid shaping member, wherein the fluid shaping member comprises at least one of a channel, rifling, boss, hump, and chamfer, or combination thereof.

21. The ablation electrode assembly of claim 1, wherein the electrode core member further includes an electrode core member outer surface facing radially outwardly, and wherein the irrigant distribution element radially outwardly surrounds at least a surrounded portion of the electrode core member outer surface to form a gap through which an irrigation fluid is permitted to flow, the gap being disposed radially outwardly from the surrounded portion of the electrode core member outer surface and radially inwardly from the irrigant distribution element.

22. The ablation electrode assembly of claim 21, wherein the gap extends circumferentially and is disposed radially inwardly from an inner surface of the irrigant distribution element, the inner surface facing radially inwardly.

23. A system for cardiac ablation of tissue, the system comprising:
- a catheter comprising:
  - a catheter shaft having a fluid lumen; and
  - an electrode assembly connected to the catheter shaft, the electrode assembly comprising:
    - an electrode core member comprising a thermal insulator having a reduced thermal conductivity, the electrode core member having:
      - a first end;
      - a second end; and
      - at least one irrigation passageway;
  - an electrode shell comprising an electrically conductive material, the electrode shell defining an inner volume and the electrode shell having:
    - a first end; and
    - a second end, wherein the second end of the electrode shell is configured for connection to the first end of the electrode core member and wherein the electrode shell is sufficiently flexible for deflection of at least a portion of the electrode shell relative to the longitudinal axis of the ablation electrode assembly;
  - an irrigant distribution element surrounding the electrode core member, the irrigant distribution element having:
    - an irrigant distribution element outer surface;
    - a first end; and
    - a second end, wherein the second end of the irrigant distribution element defines a circumferential irrigation port disposed at the irrigant distribution element outer surface between the irrigant distribution element and the electrode core member;
- at least one thermal sensor disposed within the catheter;
- an ablation generator electrically connected to at least a portion of the electrode assembly;
- an electronic control unit (ECU) operatively connected to the at least one thermal sensor, wherein the ECU is configured to receive as an input data from the at least one plurality of thermal sensors and is configured to control energy delivery and irrigation fluid delivery to the electrode assembly based at least in part on the input data.

24. An ablation electrode assembly having a longitudinal axis, the assembly comprising:
- a first electrode core member comprising a thermal insulator having a reduced thermal conductivity, the first electrode core member having:
  - a first end;
  - a second end; and
  - at least one irrigation passageway;
- a second electrode core member comprising a thermal insulator having a reduced thermal conductivity, the second electrode core member having:
  - a first end;
  - a second end; and
  - at least one irrigation passageway; and
- a first electrode shell comprising an electrically conductive material, the first electrode shell defining an inner volume and the first electrode shell having:
  - a first end configured for connection to the first end of the first electrode core member; and
  - a second end configured for connection to the first end of the second electrode core member, wherein the electrode shell is sufficiently flexible for deflection of at least a portion of the electrode shell relative to the longitudinal axis of the ablation electrode assembly.

25. The ablation electrode assembly of claim 24 further comprising:
- a first irrigant distribution element surrounding at least a portion of the first electrode core member, the first irrigant distribution element having:
  - a first end; and
  - a second end, wherein the second end of the first irrigant distribution element defines a fist circumferential irrigation port between the first irrigant distribution element and the first electrode core member; and
- a second irrigant distribution element surrounding at least a portion of the second electrode core member, the second irrigant distribution element having:
  - a first end; and
  - a second end, wherein the second end of the second irrigant distribution element defines a second circumferential irrigation port between the second irrigant distribution element and the second electrode core member.

26. The ablation electrode assembly of claim 24 further comprising a second electrode shell comprising an electrically conductive material, the second electrode shell defining an inner volume and having a first end configured for connection to the second electrode core member.

* * * * *